United States Patent [19]

Castro

[11] 4,149,276

[45] Apr. 17, 1979

[54] VENTILATED SAFETY GOGGLES

[75] Inventor: Paul Castro, Concord, Ohio

[73] Assignee: Gateway Safety Products, Brooklyn Heights, Ohio

[21] Appl. No.: 892,834

[22] Filed: Apr. 3, 1978

[51] Int. Cl.² ............................................. A61F 9/02
[52] U.S. Cl. ............................................ 2/437; 2/439; 2/441
[58] Field of Search ............... 2/436, 437, 439, 440, 2/441, 429, 426

[56] References Cited

U.S. PATENT DOCUMENTS

| 835,828 | 11/1906 | Meyrowitz | 2/437 |
| 2,430,881 | 11/1947 | Lehmberg | 2/437 |
| 2,877,463 | 3/1959 | Watkins | 2/437 |
| 3,363,262 | 1/1968 | Lindblom | 2/441 |
| 3,444,561 | 5/1969 | Boyer | 2/8 |

Primary Examiner—Peter Nerbun
Attorney, Agent, or Firm—George J. Coghill

[57] ABSTRACT

A cartridge type safety goggle for welding is disclosed having an improved ventilation system. A cover plate, gasket, filter plate and retaining spring are held in a cartridge, which is adapted to be inserted into a goggle body. A plurality of ventilating holes on the top and bottom of both the goggle body and the cartridge combine with a plurality of tabs on the cartridge to provide an air flow path which provides improved ventilation for the inside surface of the filter plate and yet prevent objectionable light from entering the interior of the goggle.

15 Claims, 4 Drawing Figures

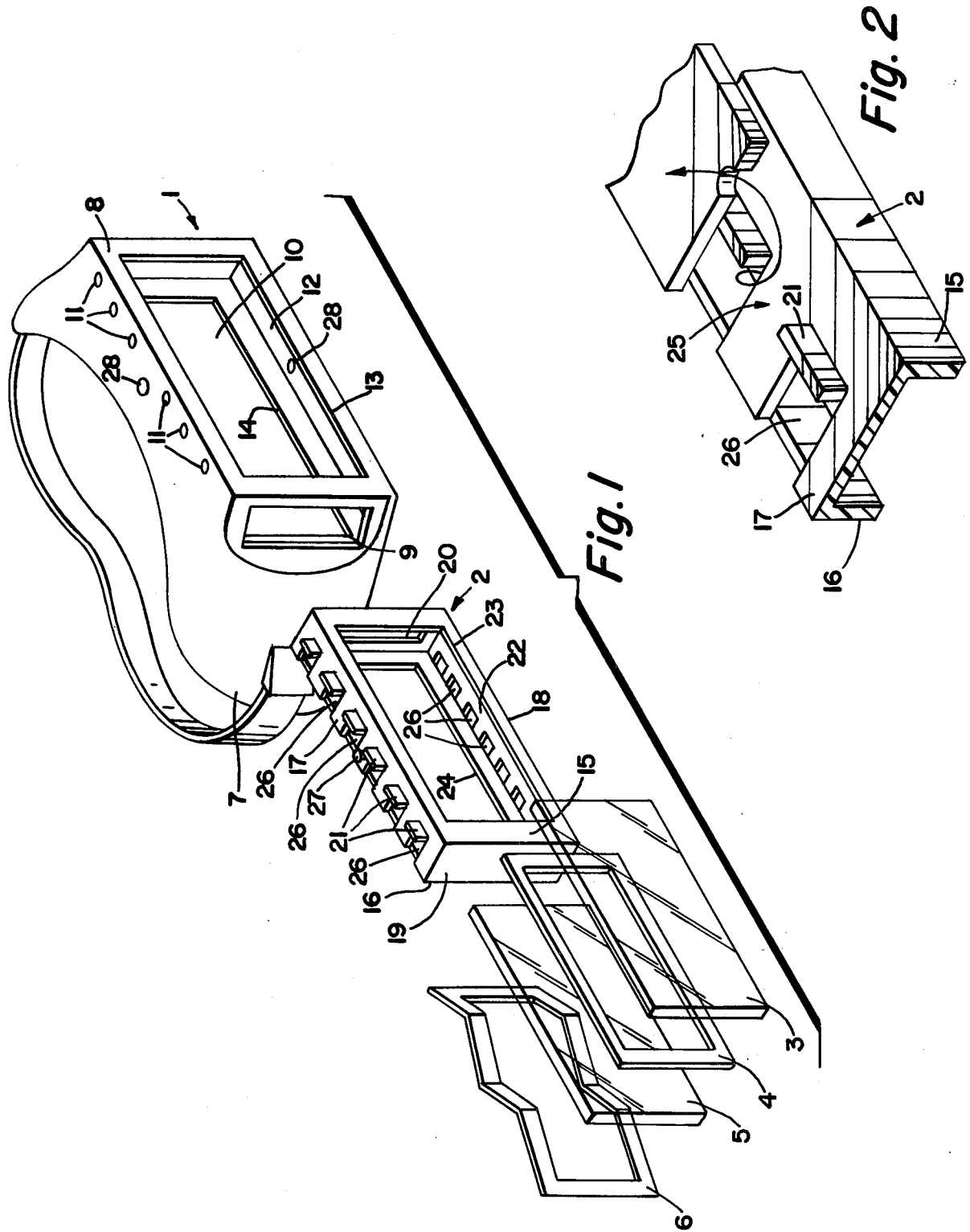

VENTILATED SAFETY GOGGLES

FIELD OF THE INVENTION

This invention relates to safety goggles, and more particularly relates to a safety goggle of the cartridge type having an improved ventilation means.

BACKGROUND OF THE INVENTION

Safety goggles are used in many industries and trades to protect a workers eyes. When workers are welding, cutting with a torch, or the like, goggles are used not only to protect the eyes from accidents resulting from particles getting into the eye, but also to protect the eyes from high intensity light emitted in the process. These types of goggles, which can be referred to generally as welders goggles, comprise of a filter plate, and usually a protective cover plate, through which the wearer views, both held in an opaque goggle body. The filter plate acts to shield the eyes from the intense light and flying particles, and the cover plate acts to protect the filter plate from flying particles.

The goggle body is generally made of an opaque pliable plastic so as to conform closely to the contour of the face. The close fit helps to assure that particles do not enter from the sides. The conforming fit also combines with the opaqueness to help assure that unfiltered light does not enter the interior of the goggle when worn. Unfiltered light entering the interior of the goggle during use, causes reflections from the rear surface of the filter plate which reduces or confuses the vision of the wearer.

Ventilation of the interior of the goggle is desireable, and almost essential, in a commercially acceptable goggle in order to allow moisture to evaporate from the interior. The moisture in the interior is caused primarily by perspiration of the skin enclosed by the goggles, and by ventilating the interior, the goggles are more confortable for the wearer. But more importantly, the ventilation reduces the tendency of the goggles to "fog up."

In the past "stack vents" were used for ventilation. These vents are well known to those skilled in the art, and essentially comprise an opening in the goggle body, generally located at the sides of the body, and covered by a cap. The shape of the cap and the opening combine to provide air passages, but yet not provide a straight-line path through which projected particles or light could pass. These stack vents do provide some measure of ventilation, but they are fairly expensive, and prior art goggles utilizing stack vents have a ventilating ability which is somewhat less than desireable.

The present invention provides a goggle which has improved ventilation, and which is less expensive to manufacture. The goggle generally comprises a goggle body, a plate holder or cartridge and a filter plate assembly. The filter plate assembly is retained in the cartridge and the cartridge is positioned in a viewing aperture in the front of the goggle body. A plurality of ventilating holes are formed along the top and bottom of the goggle body and along the top and bottom of the cartridge. When the goggle is assembled, the holes in the goggle body and the holes in the cartridge are displaced from each other. A plurality of tabs are interposed between the holes in the body and the holes in the cartridge so as to form non-straight-line or non-line-of-sight air flow paths between the holes in the body and the holes in the cartridge, thus, providing ventilation without the admission of objectionable light to the interior of the goggle.

The holes in the cartridge are located to be open to the interior of the goggle just behind the filter plate assembly. When worn, the air in the interior of the goggle is heated by the skin enclosed by the goggle. This heated air rises and passes out of the top holes, thus drawing cooler dry air in through the bottom holes. And, because of the location of the ventilating holes in the cartridge, the air drawn in at the bottom follows a flow path in close proximity to the interior surface of the filter plate assembly. This air flow across the interior surface of the filter plate assembly results in a reduced tendency of the filter plate to fog up.

BRIEF DESCRIPTION OF THE DRAWINGS

The invention can be more fully appreciated by reference to the drawing figures in which:

FIG. 1 is a perspective view of the component parts of a goggle;

FIG. 2 is a partial view of the top of a plate holder shown in FIG. 1;

DESCRIPTION OF THE PREFERRED EMBODIMENT

Figure 3:
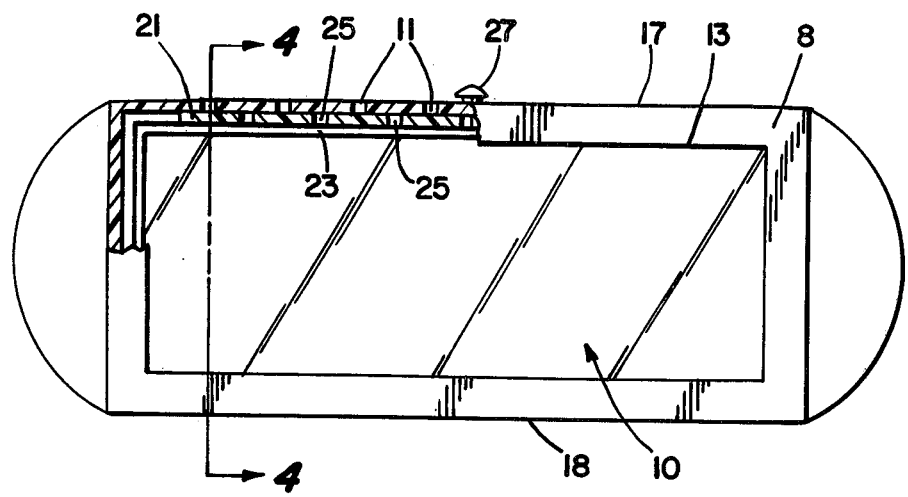
FIG. 3 is a front peel-away view of the assembled goggle components of FIG. 2.

FIG. 1 shows the component parts of a cartridge type safety goggle, comprising a goggle body 1, cartridge or plate-holder 2, a plate assembly comprising a cover plate 3, gasket 4, and filter plate 5, and a retaining spring 6. The cover plate 3, gasket 4, filter plate 5 and retaining spring 6 can be identical to those commonly used and known in the trade.

The cover plate 3 is rectangular and can be made of glass.

The gasket 4 is generally of the shape of a hollow rectangle, having outer dimensions correspond to the dimensions of the cover plate 3 and can be made from paper or other suitable gasket material. The gasket 4 serves to separate the cover plate 3 from the filter plate 5 in assembly so as to prevent contact of the two which might result in scratching. The gasket 4 also helps to keep the space between the cover plate 3 and filter plate 5 free of dirt and moisture. Preferably the gasket 4 is opaque, so as to prevent light from entering the interior of the goggle through the edge of the clear cover plate 3.

The filter plate 5 is rectangular, having the same general size and shape as the cover plate 3. The filter plate 5 can be made from glass or other suitable material known to the art. The filter plate 5 is darkened to prevent harmful light from reaching the eyes.

The retaining spring 6 is in the shape of a bent hollow rectangle, having a size generally conforming to the size of the filter plate 5, cover plate 3 and gasket 4. The spring 6 can be made of resilient plastic or spring steel.

Although the details of the cartridge 2 will be more fully discussed below, it can be generally described as being rectangular having a front rectangular face 15, a rear rectangular face 16, a top edge 17, a bottom edge 18 (hidden) and side edges 19. The cartridge 2 has a rectangular viewing aperture 29 through the front and rear rectangular faces 15, 16. A channel 22 is formed on the interior portion of the top 17, bottom 18, and sides 19 of the cartridge 2, by a front flange 23 and a rear flange 24.

The cartridge has slot 20 in one side edge 19 for inserting the cover plate 3, gasket 4, filter plate 5 and spring 6. As can be seen also in FIG. 3, the cover plate 3, gasket 4, filter plate 5 and spring 6 are held in the cartridge 2 with the cover plate 3 most forward, the gasket 4 immediately therebehind, the filter plate 5 behind the gasket 4 and the spring 6 most rearward. These items 3,4,5, and 6 are inserted into the cartridge 2 through the slot 20 on the side 19 of the cartridge 2. The cartridge 2 is fairly rigid and should be opaque enough to prevent an objectionable amount of light through it into the interior of the goggle. The surfaces of the cartridge 2, can have a matt finish to reduce any possible reflection of light.

The cartridge 2 has a plurality of tabs 21, with spaces 25 between adjacent tabs 21, on the top edge 17 and bottom edge 18. In the preferred embodiment shown, the tabs 21 are in the form of a discontinuous ridge along the top and bottom edges 17, 18 of the cartridge 2. As can be seen also in FIGS. 3 and 4 the tabs 21 contact the interior surface of the goggle body 1 and also operate to position the cartridge 2 in a viewing aperture 10 in the body 1. Button-like protrusions 27 on the top 17 and bottom 18 of the cartridge 2 cooperate with holes 28 on the body 1 to hold the cartridge 2 in the body 1.

The goggle body 1 is made of a soft plastic so as to conform the contours of the face when worn, and is opaque so that light does not enter the interior portion of the goggle. The body 1 has a strap (not numbered) attached thereto to retain the goggle on a head.

The body 1 has a rectangular viewing aperture 10. A forward flange 13 surrounds the viewing aperture 10 on the front, and a rearward flange 14 surrounds the aperture 10 at the rear, forming a channel 12 around the aperture 10 to retain the cartridge 2. The body 1 has a slot 9 in one side for inserting the cartridge 2 into the channel 12. A plurality of holes 11 are formed through the goggle body 1 on the top and on the bottom clsoe to the front, along the lateral extension of the aperture 10.

Referring briefly to FIG. 2, one additional feature of the cartridge 2 is to be noted. FIG. 2 is a partial perspective view of the top edge 17 of the cartridge 2, which can be a mirror image of the bottom edge 18. Openings 26 are formed in the cartridge 2 adjacent to and rearwardly of the tabs 21. These openings 26 establish air flow paths between the interior of the goggle and the area above or below the cartridge 2 behind the tabs 21.

FIG. 3 is a front fragmentary view of the assembled goggle. As can be seen in FIG. 3, the tabs 21 on the cartridge 2 are aligned with the holes 11 on the body 1, so as to shield the interior of the goggle from any light entering the holes 11. There are spaces 25 between successive adjacent tabs 21 which act as air flow passages from the holes 11 in the body 1 and the interior of the goggle. Thus, air entering the holes 11 in the body 1 passes sideways, around the tab 21 and through the spaces 25 between the tabs 21. The tabs 21 have a substantial length transverse to the holes 11 so as to help assure that light entering the holes 11 in the body does not have a straight-line or line-of-sight path to the interior of the goggle, and preferable not even to the space rearward of the tabs.

Thus, in operation, taking for example the top portion of the goggle, the openings 26 provide air flow from the interior of the goggle to the space above the cartridge behind the tabs 21. The spaces 25 between tabs 21 provide air flow from the area above the cartridge 2 behind the tabs 21 to the area above the cartridge 2 forward of the tabs 21. The holes 11 in the body 1 then provide air flow passage from the area above the cartridge 2 forward of the tabs 21 to the exterior of the goggle. A converse but similar operation would result at the bottom portion of the goggle.

Figure 4:
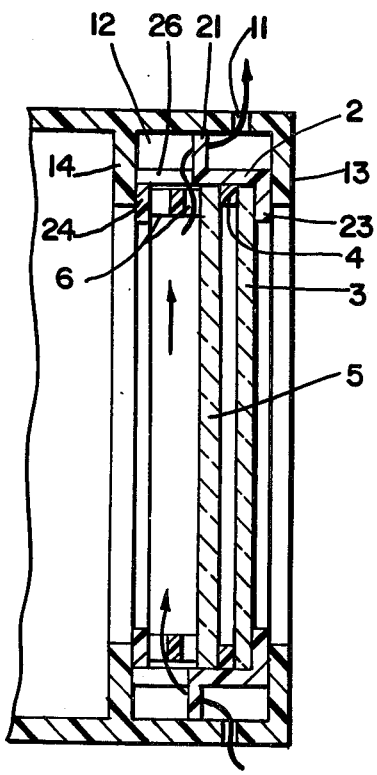
FIG. 4 is a cross sectional view of the goggle of FIG. 3 taken in a plane marked 4—4 in FIG. 3.

FIG. 4 is a cross sectional view of the assembled goggle on the plane 4–4 in FIG. 3. As can be seen in FIG. 4, the cartridge 2 is positioned in the channel 12 in the body 1. The front and rear flanges 13, 14 of the body 1 engage the front and rear of the cartridge 2 therearound, and the tabs 21 engage the interior of the body 1 at the top and bottom so as to form seals to the passage of light. The tabs 21 are positioned so as to be interposed at an intermediate position between the holes 11 in the body 1 and the openings 26 in the cartridge 2.

The cover plate 3, gasket 4, filter plate 5 and spring 6 are held between the rear flange 24 and front flange 23 on the cartridge 2, by the action of the spring tension between the rear flange 24 of cartridge 2 and filter plate 5.

The holes 11 in the body 1 can be seen to be closely adjacent the tabs 21, and in this embodiment are forward thereof.

The openings 26 in the cartridge 2 can be seen to be generally in the plane of the spring 6. These openings 26 are located closely rearwardly of the plane of the filter plate 5 so that air flow in the interior of the goggle passes from the openings 26 at the bottom, and is directed in a path close to the inside or rear surface of the filter plate 5, to the openings 26 at the top so as to provide good ventilation to the surface of the filter plate 5.

It will be appreciated by those skilled in the art that modifications can be made to the preferred embodiment without departing from the invention. For example, the placement of the holes, tabs, openings and air passages can be modified either alone or in combination without departing from the invention. Certain aspects of the invention also have application to other plate type safety goggles such as the "flip-front" types. Other details, common to goggles in general can be changed without departing from the invention.

Therefore, it is intended that the invention only be limited by the following claims wherein

I claim:

1. A ventilated goggle comprising:
   an opaque goggle body having a top and bottom portion and an interior having a viewing aperture at the front, a plurality of holes through said body along its top and bottom above and below said aperture, and being adapted to have a cartridge type plate assembly in said aperture;
   an opaque cartridge having a top portion and bottom portion, and having a plate assembly therein, and being located in said viewing aperture and having openings along its top and bottom effective to establish air flow communication with said interior portion of said goggle body; and
   a plurality of opaque tabs along the top and bottom of the cartridge and between the cartridge assembly and the goggle body, said tabs being located adjacent said holes in the goggle body, and said tabs forming air passages between adjacent ones being effective to communicate air flow from said holes in said body to said openings in said cartridge.

2. The goggle of claim 1 wherein said tabs along the top of said cartridge are in contact with both the goggle body and with the top of said cartridge; and said tabs along the bottom of said cartridge are in contact with the bottom of said cartridge and with said body.

3. The goggle of claim 1 wherein said plurality of tabs comprise discontinuous ridges formed on the top and bottom of said cartridge.

4. The goggle of claim 2 wherein said tabs have a substantial side to side dimension transverse to said holes in said body and said openings in said cartridge.

5. The goggle of claim 4 wherein said openings in said cartridge are adjacent said tabs.

6. The goggle of claim 5 wherein said openings in said cartridge comprise a plurality of individual openings which are laterally aligned with said holes in said body but wherein said openings in said cartridge are displaced rearwardly from said holes in said body, and wherein said tabs are located at an intermediate position between said holes and said openings.

7. The goggle of claim 6 wherein the plate assembly comprises
 a filter plate; and
 a spring located rearwardly adjacent said filter plate; and
 wherein said openings in said cartridge are located in the plane of said spring.

8. The goggle of claim 3 wherein said tabs are aligned with said holes in said body across said goggle and wherein said tabs are located closely rearward of said holes in said body.

9. The goggle of claim 8 wherein said openings in said cartridge, comprise a plurality of individual openings adjacent said tabs, and are located closely rearward of said plate assembly.

10. The goggle of claim 8 wherein said tabs have a substantial lateral dimension transverse to said holes in said body.

11. The goggle of claim 10 wherein said tabs form non-line-of-sight air passages which communicate air flow between said openings in said cartridge and said holes in said body.

12. The goggle of claim 11 wherein said openings in said cartridge are located closely rearward of said plate assembly.

13. The goggle of claim 10 wherein said goggle body further comprises a channel which retains said cartridge.

14. The goggle of claim 13 wherein said openings in said cartridge are located closely rearward of said plate assembly.

15. The goggle of claim 14 wherein said plate assembly comprises:
 a cover plate located most forwardly;
 a filter plate rearward of said cover plate;
 a gasket between said cover plate and said filter plate; and
 wherein said goggle further comprises a spring rearward of said filter plate effective to retain said plate assembly firmly in said cartridge.

* * * * *